United States Patent [19]
Nakagawa et al.

[11] Patent Number: 6,140,311
[45] Date of Patent: *Oct. 31, 2000

[54] THERAPY BY INTRATHECAL ADMINISTRATION OF ANTITUMOR AGENT FUDR

[75] Inventors: Hidemitsu Nakagawa, Sakai; Masanobu Yamada, Itami; Kazuhiro Ikenaka, Okazaki, all of Japan

[73] Assignee: Taiho Pharmaceutical Company, Limited, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/788,841

[22] Filed: Jan. 27, 1997

[51] Int. Cl.⁷ ..................................................... A61K 31/70
[52] U.S. Cl. .............................................................. 514/50
[58] Field of Search ................................................ 514/50

[56] References Cited

U.S. PATENT DOCUMENTS 5,455,044  10/1995  Kim et al. .............................. 424/450

OTHER PUBLICATIONS

Cancer vol. 68, 995–998 (1991)–B.Damascelli et al.

*Primary Examiner*—Kimberly Jordan
*Attorney, Agent, or Firm*—Arent Fox Kintner Plotkin & Kahn

[57] ABSTRACT

The invention relates to a novel method of treating malignant brain tumors and meningeal dissemination of malignant tumors by intrathecally giving FUDR, an antitumor agent, to produce an outstanding therapeutic effect selectively on the tumor cells with safety.

13 Claims, 7 Drawing Sheets

(4 of 7 Drawing Sheet(s) Filed in Color)

Fig. 4K          Fig. 4J          Fig. 4L though the compound was clinically applied to glioblastoma and metastatic brain tumors by intravenous administration in a very few cases, the results achieved have yet to be established as standard therapeutic effects (Cancer 68:995–98, 1991).

THERAPY BY INTRATHECAL ADMINISTRATION OF ANTITUMOR AGENT FUDR

TECHNICAL FIELD

The present invention relates to a method of treating malignant brain tumors and meningeal dissemination of malignant tumors more effectively with exceedingly higher safety than conventional therapies, using 5-fluoro-deoxyuridine (FUDR), an antitumor agent, which exhibits antitumor activity selectively on the cancer cells.

BACKGROUND ART

The number of deaths from cancers is ever increasing in the U.S. year by year and-will presumably exceed 600,000 in 1996. About 24% of these deaths are-attributable to brain tumors and the metastases of various primary tumors to the brain. Since the metastasis entails hyper intracranial pressure and dysfunction of the brain, metastatic brain tumors are a major cause of the deaths from cancers (Rev. Neurol. (Paris) 148:477–487, 1992). Especially, approximately 5% of various solid cancers, such as lung cancer, breast cancer and colon cancer, are thought to develop into meningeal carcinomatosis when metastasizing to the brain. Cancer patients tend to develop this disease more frequently in recent years with increases in the survival time.

Among other metastatic brain tumors, meningeal carcinomatosis in particular results from meningeal irritation due to tumors, impeded circulation of CSF due to obstruction of the CSF pathway, infiltration of tumors into the cerebrospinal parenchyma, and infiltration of tumors into the cranial nerves or spinal nerves extending through the subarachnoid cavity, therefore presenting a wide variety of seriously aggravated lethal symptoms including headaches, encephalopathies, dyskinesia and sensory disturbances.

Meningeal carcinomatosis is treated generally by intrathecal administration of anticancer agents, topical application of radiation or the combination of both. For example, methotrexate (MTX) is usually intrathecally given singly or in combination with Cytosine Arabinoside (Ara-C) via an Ommaya reservoir placed in the lateral ventricle (Arch Neurol. 38:696–699, 1981, Cancer 49:219–222, 1982, Cancer 49:759–72, 1982, Neurology 33:1565–72, 1983, J. Clinical Ankle. 4.68–73, 1986, Clinical Oncol. 5:1655–62, 1987). The intrathecal administration of these anticancer agents achieves a therapeutic efficacy of about 40 to about 60%, clinically leads to temporary regression for a short period in some cases but fails to improve the usual performance status in other cases despite regression. Acute neurotoxicity and retarded necrotizing encephalopathy, side effects of MTX in prevalent use, impose limitations on the dose which is sufficient to clinically produce a satisfactory therapeutic effect, with the result that the effect achieved still remains to be improved (New England J. Med. 289:770–73, 1973).

FUDR for use in the present invention is an active metabolite of 5-fluorouracil (5-FU) and a known compound which has very high antitumor activity and which is used in the U.S. as a drug for treating the metastasis of colon cancer to the liver (Ann. Surg., 206:685–693, 1987, Ann. Intern. Med., 107:459–465, 1987, J. Clinical Oncol., 7:1646–1654, 1989, Arch. Surg., 125:1022, 1990, J. Clinical Oncol., 10:1112–1118, 1992, J. Clinical Oncol., 8:1885–1893, 1990, Lance, 344:1255–1260, 1994). Although the compound was clinically applied to glioblastoma and metastatic brain tumors by intravenous administration in a very few cases, the results achieved have yet to be established as standard therapeutic effects (Cancer 68:995–98, 1991).

Accordingly, in view of the current therapies for patients with metastatic brain tumors, especially with meningeal carcinomatosis, it is desired to develop a safe and effective method of treatment with QOL (quality of life) of the patient taken into consideration.

DISCLOSURE OF THE INVENTION

In the light of the present situation described, we have conducted intensive research and found that when intrathecally given, the antitumor agent, FUDR, produces a remarkable therapeutic effect on malignant brain tumors and the meningeal dissemination of malignant tumors without exhibiting toxicity although the agent has not been clinically applied to these diseases. The present invention has been accomplished based on this finding.

More specifically, the present invention provides a novel method of treatment by the intrathecal administration of FUDR which exhibits an outstanding antitumor effect without permitting the treatment to produce side effects such as neurotoxicity and toxicity to the digestive tracts, based on the biochemical differences between the activity of FUDR metabolizing enzymes on normal brain tissues and that of the enzymes on tumor cells which are responsible for malignant brain tumors and for meningeal dissemination of malignant tumors.

The present invention provides a method of treating malignant brain tumors and meningeal dissemination of malignant tumors by the intrathecal administration of FUDR.

FUDR is metabolized in vivo by thymidine kinase (TK) and converted to 5-fluoro-2'-deoxyuridine-5'-monophosphate (FdUMP), which inhibits thymidylate synthase (TS), a key enzyme in DNA synthesis, to exhibit high cytotoxicity. On the other hand, FUDR is anabolized to 5-FU by thymidine phosphorylase (TPase) and thereby diminished in its antitumor effect (Biochemistry 2:566–572, 1963, Cancer Res. 18:335–34–3, 1985, J. Biol. Chem. 236:3006–3018, 1961, Biochem. Biophys. Res. Commun. 48:1565–1972, Proc. Natl. Acad. Sci. USA 69:1855–1972). In causing FUDR to exhibit its efficacy, therefore, it is critical to give consideration to the balance between the activity of these enzymes in tumor tissues and the activity thereof in normal tissues.

Accordingly we investigated the activity of the FUDR metabolizing enzymes on brain tumors such as malignant glioma and metastatic meningeal carcinomatosis, normal tissues of the stomach, colon, lung, liver, brain, CSF, etc., and normal brain tissues, and found that TK activity which results in cytotoxicity is higher in malignant glioma and metastatic brain tumors than in the other normal tissues and that TPase activity which serves to mitigate cytotoxicity is lower in malignant glioma and metastatic brain tumors than in the normal brain tissue (Intern. Cong. Anti-Cancer Treat. 6:205, 1996 (Abstract)).

Based on the biochemical differences between the FUDR metabolizing enzymes, the present invention therefore provides a method of treating patients with malignant brain tumors or with meningeal dissemination of malignant tumors by the intrathecal administration of FUDR to achieve an excellent antitumor effect without permitting the treatment to produce any toxic effect.

Figure 1:
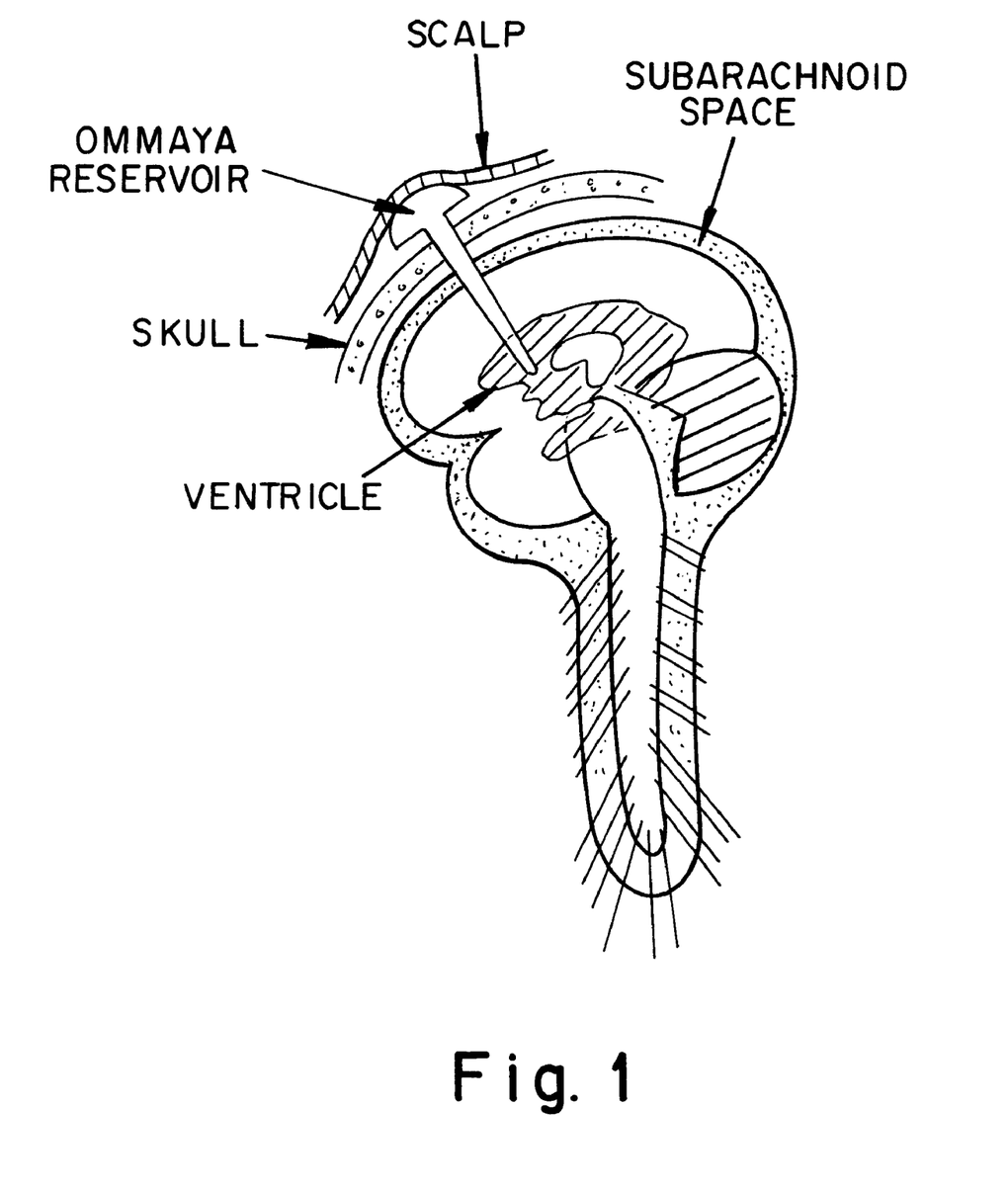
FIG. 1 shows an Ommaya reservoir placed in the anterior horn.

The antitumor agent of the invention, FUDR, is given using-an Ommaya reservoir (FIG. 1) which is in common use for intrathecally administering drugs for meningeal carcinomatosis (Lancet 2: 983–84, 1963). More specifically, a ventricular tube inserted through a hole formed in the anterior horn is connected to an Ommaya reservoir installed under the scalp, and the reservoir is subcutaneously punctured to intrathecally give FUDR injected into the reservoir. Alternatively, the drug may be intrathecally given, for example, by a single injection, continuous infusion or ventriculolumbar perfusion.

The compound FUDR to be given by the present method is preferably in the form of an injection as a unit of administration. Examples of carriers usable for preparing injections include diluents such as water, ethyl alcohol, macrogol, propylene glycol, ethoxylated isostearyl alcohol, polyoxyisostearyl alcohol and polyoxyethylene sorbitan fatty acid esters, pH adjusting agents or buffers such as sodium citrate, sodium acetate and sodium phosphate, stabilizers such as sodium pyrosulfite, EDTA, thioglycolic acid and thiolactic acid, isotonic agents such as sodium chloride and glucose, local anesthetics such as procaine hydrochloride and lidocaine hydrochloride. Furthermore usual solubilizing agents and analgesics may be added. Injections can be prepared by adding such carriers to the active compound, followed by the usual procedure.

The method of giving FUDR and the dose thereof according to the invention can not be determined straightforwardly but may vary with the symptoms, body weight, age and sex of the patient. The single dose of FUDR is usually about 0.1 to about 1000 $\mu$g/body, preferably 0.5 to 20 $\mu$g/body, for adults. It is desirable to give the dose once to three times a day, give the daily dose or doses once to seven times a week and repeat this mode of administration for 3 weeks to 6 months. It is desired that the amount of FUDR per unit of administration, which is suitably determined, be usually 0.1 $\mu$g to 100 $\mu$g.

The malignant tumors to be treated according to the present invention are not limited particularly in type insofar as they are intraventricular or meningeal metastases which are sensitive to FUDR. Examples of such tumors are cases of meningeal dissemination developing from glioblastoma, lung cancer, breast cancer, stomach cancer, colon cancer, rectum cancer, liver cancer, bladder cancer, malignant melanoma, leukemia and malignant lymphoma. The present method can be expected to achieve outstanding therapeutic effects especially on meningeal metastases resulting from glioblastoma, lung cancer, breast cancer, colon cancer and rectum cancer.

BRIEF DESCRIPTION OF DRAWINGS

The file of this patent contains at least one drawing executed in color. Copies of this patent with color drawings are provided to the Patent and Trademark Office with payment of the necessary fee.

In FIGS. 2 and 3, FUDR is shown as FdUrd.

BEST MODE OF CARRYING OUT THE INVENTION

The present invention will be described in greater detail with reference to the following experimental examples.

EXPERIMENTAL EXAMPLE 1

In Vivo Antitumor Effect of FUDR given by Present Method

Six-week-old C57/BL6 mice divided into groups of 22 or 23 were used to prepare models of meningeal carcinomatosis by directly puncturing the cisterna magna with a 26-gauge needle under anesthesia with ethyl ether and injecting transplantable 203 glioma cells ($5 \times 10^5$ cells/0.05 ml). The mice were given a specified dose of FUDR by intrathecal injection (0, 25, 50, 100 or 250 $\mu$g/0.05 ml/head) daily for 5 consecutive days following the day of transplant.

Figure 2:
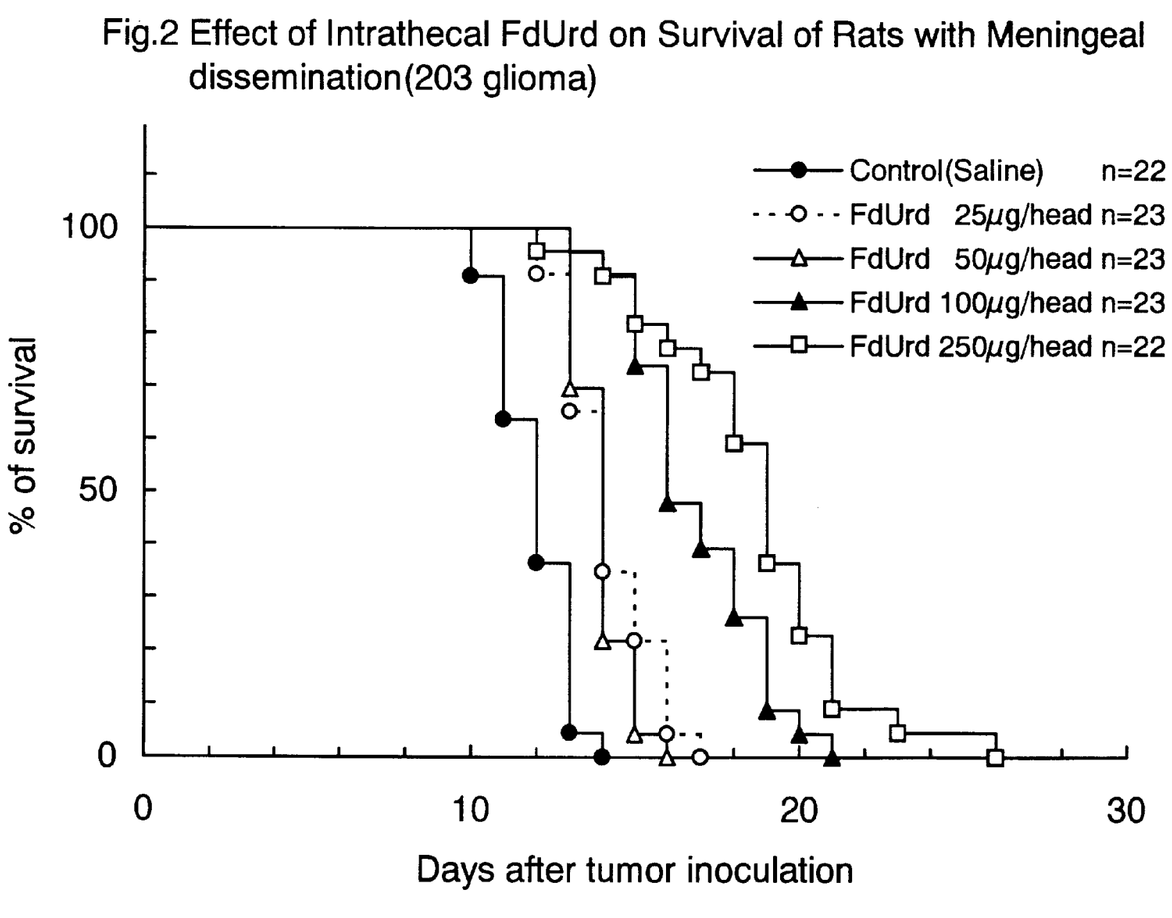
FIG. 2 shows effect of intrathecal FUDR on survival of rats with meningeal dissemination.

FIG. 2 shows the results obtained. On day 14 postimplantation, the control group (given 0.05 ml of physiological saline) were all found dead, whereas the group given 250 $\mu$g/0.05 ml of FUDR and the group with 100 $\mu$g/0.05 ml exhibited a significantly prolonged survival effect, with 21 survivors among 22 animals.

EXPERIMENTAL EXAMPLE 2

Toxicity of FUDR given by the Present Method

Normal C57/BL6 mice divided into groups of 20 were given FUDR by intrathecal injection at a specified dose (0, 10, 25, 50 or 100 $\mu$g/0.05ml/head) on the day of start of the experiment, 2 days, 4 days and 6 days after the start. Two months after the completion of administration of the drug, the mice were all sacrificed, and brain tissues were collected, followed by hematoxylin & eosin staining and Kluver Barrera staining for histological investigation.

Figure 3:
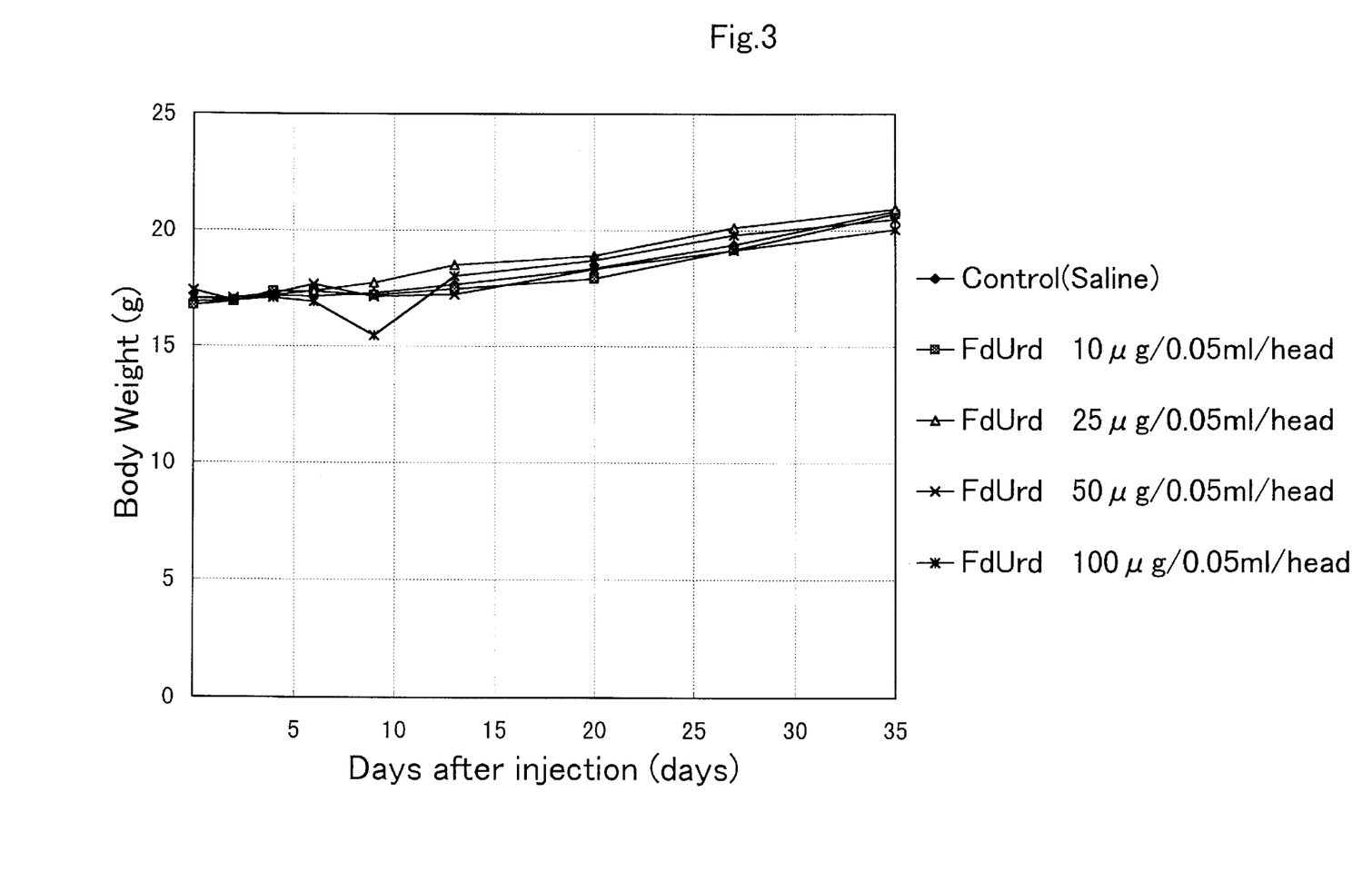
FIG. 3 shows body weight variations of mice used in Experimental Example 2.
Figure 4A:
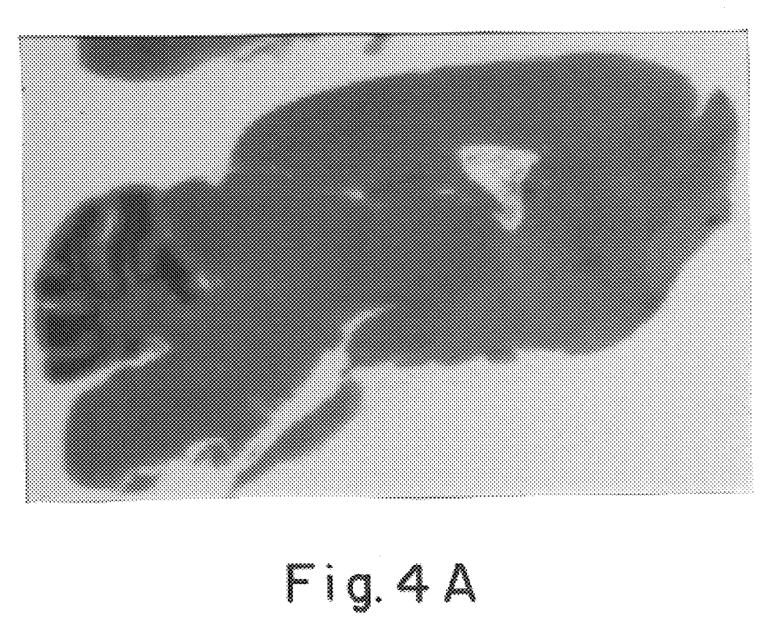
FIGS. 4A–4L show histological brain tissues as stained of mice used in Experimental Example 2.
Figure 4B:
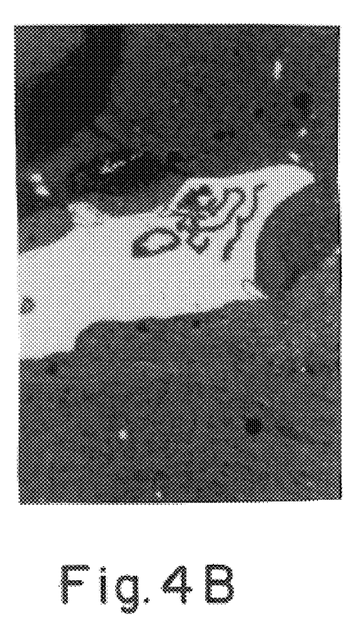
Figure 4C:
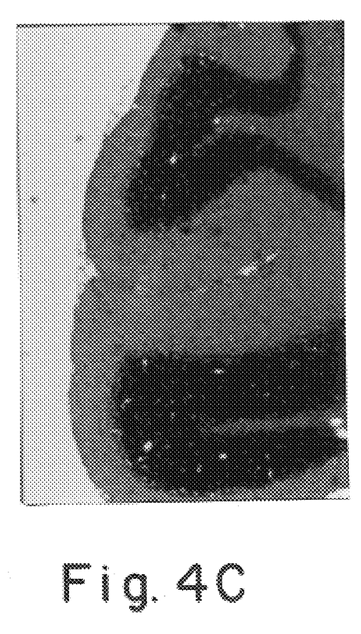
Figure 4D:
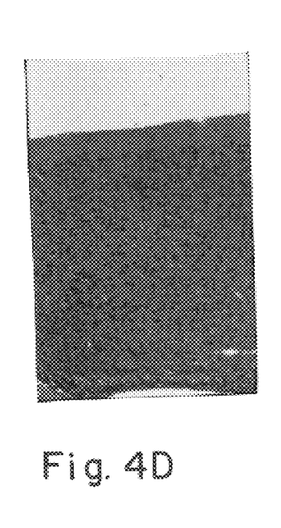
Figure 4E:
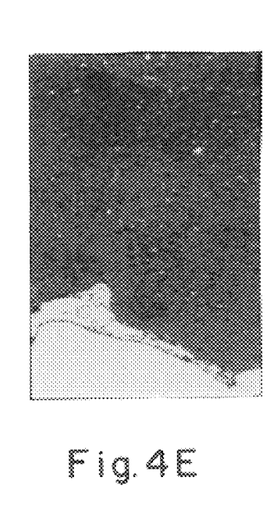
Figure 4F:
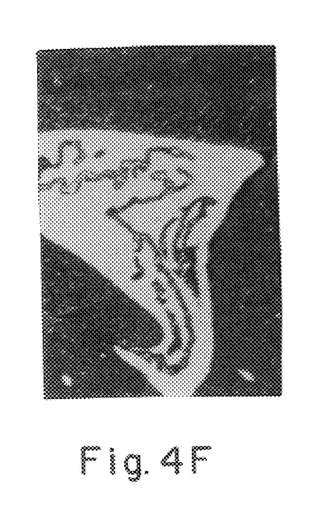
Figure 4G:
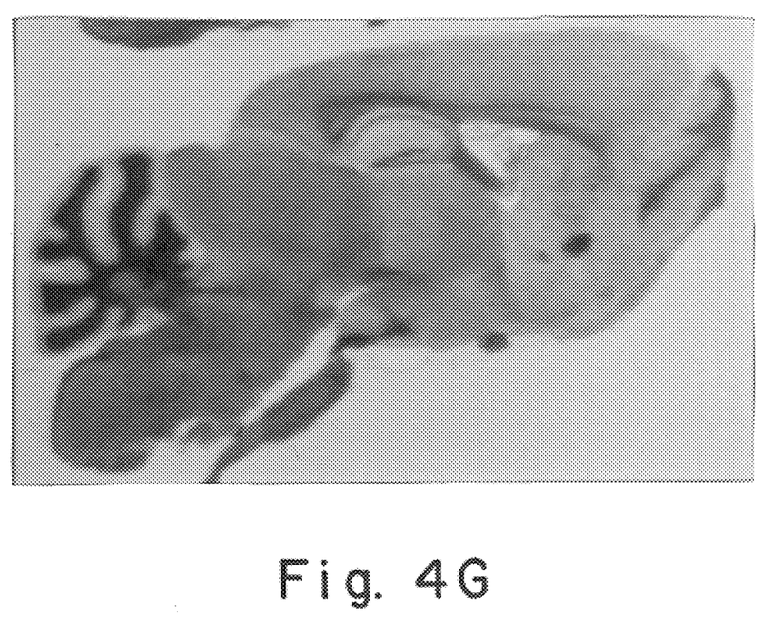
Figure 4H:
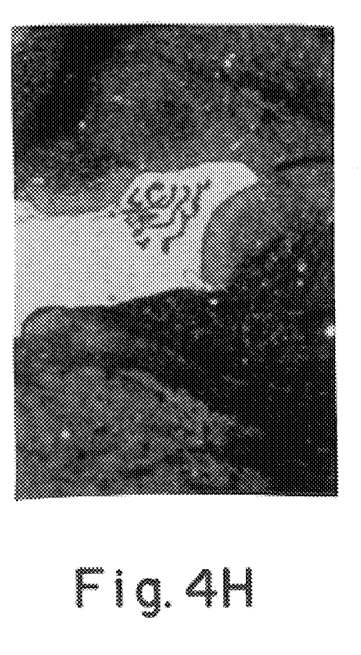
Figure 4I:
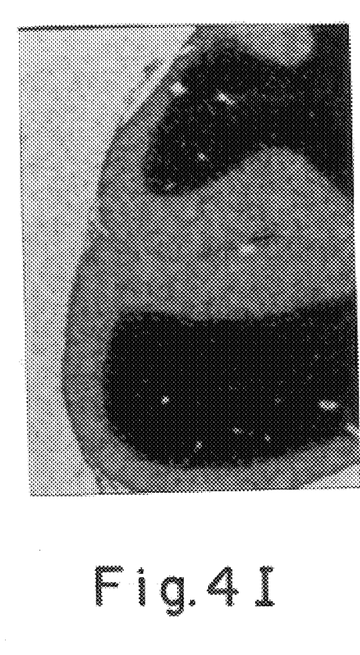
Figure 4J:
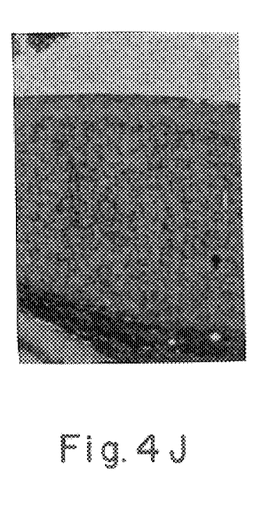
Figure 4K:
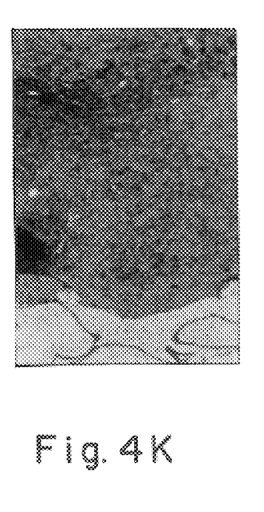
Figure 4L:
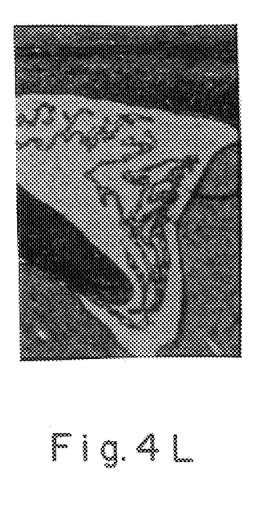

The results obtained are shown in FIG. 3 (body weight variations) and FIGS. 4A–4L (histological brain tissues as stained). With reference to FIG. 3, the high-dose group (100 $\mu$g/0.05 ml) showed a transient weight decrease after the completion of administration, but recovery followed on the next day of weight loss. The group was found free of side effects such as frequent diarrhea experienced with intravenous administration of FUDR. The medium-dose group (50 $\mu$g/0.05 ml) and small-dose groups (25 $\mu$g/0.05 ml, 10 $\mu$g/0.05 ml) exhibited no weight decrease whatever. Furthermore, none of the mice developed neurotic manifestation during and after the period of administration of FUDR.

FIGS. 4A–4L show examples of histological changes in cranial nerve tissues of the high-dose (2 $\mu$g/ml) group. FIGS. 4A–4F show hematoxylin & eosin staining. FIGS. 4G–4L show Kluver Barrera staining. The result indicates that none of the mice exhibited abnormalities in the cranial nerve tissues, such as rupture of the lining of ventricular ependymal cells in the vicinity of the site of administration, decrease in the number of neuronal cells and demyelination. The medium-dose group and the small-dose groups gave the same result as above.

EXPERIMENTAL EXAMPLE 3

Clinical Results

FUDR was intrathecally administered with use of an Ommaya reservoir to 13 patients having meningeal dissemination of various primary-tumors and admitted to the Osaka Medic Center for Cancer & Cardiovascular Diseases. The drug was given at a dose of 1 to 10 $\mu$g/body a day, three times a week. The period of administration was varied from 3 to 8 weeks in accordance with the symptoms of the disease.

Table 1 shows the results, revealing none of side effects such as toxicity to the digestive tracts, neurotoxicity, myelosuppression, and dysfunction of the liver and kidney and indicating diminutions of tumor marker, CSF cells and protein in CSF, hence efficacy of the drug. These results substantiate that the therapy of the invention can be practiced with safety without producing any systemic influence and affecting the cranial nerve tissues.

TABLE 1

Clinical results of intrathecal chemotherapy with FUDR in patients with meningeal dissemination of malignant tumours

| No. of patients | Origin | Response on CSF findings | CSF Tumor marker | Cell numbers (/mm³) | | Protein (mg/dl) | | Side effects |
| --- | --- | --- | --- | --- | --- | --- | --- | --- |
| | | | | Ventricular CSF* | Spinal CSF** | Ventricular CSF* | Spinal CSF** | |
| 1 | Lung | Response | — | 1238→96 | 12→7 | 540→249 | 95→68 | None |
| 2 | Lung | Response | CEA 2530→1065 | 23→9 | 39→26 | 147→76 | 197→132 | None |
| 3 | Lung | Response | NSE 13.7→5.2 | 4→2 | 14→8 | 27→18 | 60→6 | None |
| 4 | Unknown | Response | NSE 12.1→5.1 | 1658→1 | 31→2 | 78→40 | 62→43 | None |
| 5 | Lung | Response | NSE 19.0→6.2 | 252→8 | 177→31 | 205→17 | 133→29 | None |
| 6 | Lung | Response | CEA 382→13.3 | 4→2 | 82→3 | 7→17 | 450→19 | None |
| 7 | Breast | No Response | CA125 134→36 | 53→12 | 342→520 | 172→206 | 694→2400 | None |
| 8 | Lung | No Response | CEA 28→19.4 | 24→33 | 18→13 | 24→126 | 38→231 | None |
| 9 | Colon | Response | CEA 239→19.7 | 41→2 | 161→9 | 43→12 | 230→271 | None |
| 10 | Brain | No Response | — | 50→44 | 16→25 | 2010→1400 | 234→198 | None |
| 11 | Unknown | Response | NSE 11.3→7.4 | 38→10 | 39→24 | 230→74 | 259→108 | None |
| 12 | Colon | Response | CEA 121.6→<1.0 | 8→7 | 144→8 | 67→47 | 136→84 | None |
| 13 | Lung | Response | CEA 13.9→2.6 | 78→7 | 83→7 | 82→19 | 113→80 | None |

CEA (ng/ml); carcinoembryonic antigen,
NSE (U); neuron specific enolase,
CA125 (U); carbohydrate antigen 125
*CSF obtained by anterial horn of lateral ventricle,
**CSF obtained by lumbar puncture A preparation examples of the invention is given below.

PREPARATION EXAMPLE 1

Injection

An injection of the following composition was prepared by the usual procedure.

| FUDR | 1.0 mg |
| --- | --- |
| Physiological saline | suitable amount |
| Contents per ampule | 2 ml |

EFFECT OF THE INVENTION

The therapy of the invention by intrathecal administration of the antitumor agent FUDR is very effective for-treating metastatic brain tumors and meningeal carcinomatosis. Moreover, the method of -the invention has the remarkable advantage; of producing no side effects, exerting no influence on the whole-body and cranial nerve tissues and assuring safety.

What is claimed is:

1. A method for treating meningeal dissemination of metastatic brain tumor developing from glioblastoma, lung cancer, breast cancer, stomach cancer, colon cancer, rectum cancer, liver cancer, bladder cancer, malignant melanoma, leukemia or malignant lymphoma in a mammal, comprising intrathecally administering 5-fluoro-deoxyuridine to a mammal in need of such treatment without side effects, wherein 5-fluoro-deoxyuridine is administered at a dose of about 0.1 to about 1000 μg/body one to three times per day.

2. A method as defined in claim 1 wherein the brain tumor is a meningeal dissemination of a metastatic brain tumor.

3. A method as defined in claim 1 wherein 5-fluoro-deoxyuridine is administered by injection, continuous infusion or ventriculolumbar perfusion.

4. A method as defined in claim 1 wherein a dose of 5-fluoro-deoxyuridine is given once a day, once to 7 times a week, and this schedule is repeated for 3 weeks to 6 months.

5. The method of claim 1 wherein said side effects are neurotoxicity or toxicity to the digestive tracts.

6. The method of claim 1, wherein 5-fluoro-deoxyuridine is administered at a dose of about 0.1 to about 1000 μg/body once per day.

7. The method of claim 1 wherein 5-fluoro-deoxyuridine is administered at a dose of about 0.5 to about 20 μg/body one to three times per day.

8. The method of claim 7 wherein 5-fluoro-deoxyuridine is administered at a dose of about 0.5 to about 20 μg/body once per day.

9. A method of treating meningeal dissemination of metastatic brain tumor developing from glioblastoma, lung cancer, breast cancer, stomach cancer, colon cancer, rectum cancer, liver cancer, bladder cancer, malignant melanoma, leukemia or malignant lymphoma in a mammal comprising intrathecally administering a solution consisting essentially of 5-fluoro-deoxyuridine and one or more components selected from the group consisting of diluents, pH adjusting agents, buffers, stabilizers, isotonic agents, local anesthetics, solubilizing agents and analgesics to a mammal in need of such treatment without side effects, wherein 5-fluoro-deoxyuridine is administered at a dose of about 0.1 to about 1000 μg/body one to three times per day.

10. The method of claim 9 wherein said side effects are neurotoxicity or toxicity to the digestive tracts.

11. The method of claim 9, wherein 5-fluoro-deoxyuridine is administered at a dose of about 0.1 to about 1000 μg/body once per day.

12. The method of claim 9 wherein 5-fluoro-deoxyuridine is administered at a dose of about 0.5 to about 20 μg/body one to three times per day.

13. The method of claim 12 wherein 5-fluoro-deoxyuridine is administered at a dose of about 0.5 to about 20 μg/body once per day.

* * * * *